United States Patent
King

(10) Patent No.: US 7,206,632 B2
(45) Date of Patent: Apr. 17, 2007

(54) PATIENT SENSORY RESPONSE EVALUATION FOR NEUROMODULATION EFFICACY RATING

(75) Inventor: Gary W. King, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 455 days.

(21) Appl. No.: 10/768,352

(22) Filed: Jan. 30, 2004

(65) Prior Publication Data

US 2005/0075669 A1 Apr. 7, 2005

Related U.S. Application Data

(60) Provisional application No. 60/508,354, filed on Oct. 3, 2003, provisional application No. 60/508,318, filed on Oct. 2, 2003.

(51) Int. Cl.
*A61B 5/00* (2006.01)
(52) U.S. Cl. .................. 600/544; 600/554; 600/545; 607/2
(58) Field of Classification Search ........... 600/544, 600/545, 552–555; 607/2
See application file for complete search history.

(56) References Cited

U.S. PATENT DOCUMENTS

| | | | |
|---|---|---|---|
| 4,305,402 A | 12/1981 | Katims | |
| 4,503,863 A | 3/1985 | Katims | |
| 4,557,271 A | 12/1985 | Stoller et al. | |
| 4,570,640 A | 2/1986 | Barsa | |
| 4,640,266 A | 2/1987 | Levy | |
| 5,018,526 A | 5/1991 | Gaston-Johansson | |
| 5,191,896 A | 3/1993 | Gafni et al. | |
| 5,233,984 A | 8/1993 | Thompson | |
| 5,370,672 A | 12/1994 | Fowler et al. | |
| 5,388,587 A | 2/1995 | Knutsson et al. | |

(Continued)

FOREIGN PATENT DOCUMENTS

EP 0 236 513 9/1987

(Continued)

OTHER PUBLICATIONS

Notification of Transmittal of the International Preliminary Examination report dated Oct. 24, 2005, International Application No. PCT/US2004/029851, (10 pages).

(Continued)

*Primary Examiner*—Charles Marmor, II
(74) *Attorney, Agent, or Firm*—Shumaker & Sieffert, PA

(57) ABSTRACT

The invention is directed to a technique for rating neuromodulation efficacy based on evaluation of the response of the patient to sensory stimuli with and without delivery of neuromodulation therapy. In addition, the invention may provide a system capable of delivering sensory stimuli on a quantitative basis in a coordinated manner with delivery of neuromodulation therapy. A device programmer may provide a platform for controlling delivery of the sensory stimuli, delivery of neuromodulation therapy, and generation of rating information for neuromodulation efficacy based on patient sensory response to the stimuli. In operation, the programmer controls application of selected sensory stimuli to the patient's body and records the patient's verbal or physiological responses to the stimuli. This invention can be used to be a diagnostic or prognostic test that a given neuromodulation therapy, such as neurostimulation or drug delivery, is and will be successful.

41 Claims, 9 Drawing Sheets

U.S. PATENT DOCUMENTS

| | | | |
|---|---|---|---|
| 5,433,211 A | 7/1995 | Brammer et al. | |
| 5,443,486 A | 8/1995 | Hrdlicka et al. | |
| 5,692,500 A | 12/1997 | Gaston-Johansson | |
| 5,725,472 A | 3/1998 | Weathers | |
| 5,797,854 A | 8/1998 | Hedgecock | |
| 5,806,522 A | 9/1998 | Katims | |
| 5,814,092 A | 9/1998 | King | |
| 5,893,881 A | 4/1999 | Elsberry et al. | |
| 5,913,882 A | 6/1999 | King | |
| 5,938,690 A * | 8/1999 | Law et al. | 607/46 |
| 5,941,833 A | 8/1999 | Lipman | |
| 6,018,682 A | 1/2000 | Rise | |
| 6,027,456 A | 2/2000 | Feler et al. | |
| 6,113,552 A | 9/2000 | Shimazu et al. | |
| 6,146,334 A | 11/2000 | Laserow | |
| 6,249,703 B1 | 6/2001 | Stanton et al. | |
| 6,308,102 B1 | 10/2001 | Sieracki et al. | |
| 6,315,736 B1 | 11/2001 | Tsutsumi et al. | |
| 6,337,997 B1 | 1/2002 | Rise | |
| 6,366,813 B1 | 4/2002 | DiLorenzo | |
| 6,418,344 B1 | 7/2002 | Rezai et al. | |
| 6,473,653 B1 | 10/2002 | Schallhorn et al. | |
| 6,537,231 B1 | 3/2003 | Teich et al. | |
| 6,547,746 B1 * | 4/2003 | Marino | 600/554 |
| 6,612,983 B1 | 9/2003 | Marchal | |
| 6,615,081 B1 * | 9/2003 | Boveja | 607/2 |
| 6,644,321 B1 | 11/2003 | Behm | |
| 6,647,299 B2 | 11/2003 | Bourget | |
| 6,654,642 B2 | 11/2003 | North et al. | |
| 6,702,767 B1 | 3/2004 | Douglas et al. | |
| 2001/0007950 A1 | 7/2001 | North et al. | |
| 2002/0107434 A1 | 8/2002 | Lange et al. | |
| 2002/0111754 A1 | 8/2002 | Lange et al. | |
| 2002/0128798 A1 | 9/2002 | Lange et al. | |
| 2002/0147485 A1 | 10/2002 | Mamo et al. | |
| 2002/0177882 A1 | 11/2002 | DeLorenzo | |
| 2003/0105413 A1 | 6/2003 | Bleustein et al. | |
| 2003/0139785 A1 | 7/2003 | Riff et al. | |
| 2003/0171789 A1 | 9/2003 | Malek et al. | |
| 2003/0204148 A1 | 10/2003 | Lange et al. | |
| 2004/0006377 A1 | 1/2004 | Behm | |
| 2004/0059395 A1 | 3/2004 | North et al. | |
| 2004/0079372 A1 | 4/2004 | John et al. | |
| 2004/0098063 A1 | 5/2004 | Goetz | |
| 2006/0122660 A1 * | 6/2006 | Boveja et al. | 607/40 |

FOREIGN PATENT DOCUMENTS

| | | |
|---|---|---|
| EP | 0 364 158 | 4/1990 |
| EP | 0 438 541 | 7/1991 |
| EP | 0 530 354 | 3/1993 |
| EP | 0 892 654 | 1/1999 |
| GB | 2 049 431 | 12/1980 |
| WO | WO 91/16001 | 10/1991 |
| WO | WO 92/10134 | 6/1992 |
| WO | WO 96/01665 | 1/1996 |
| WO | WO 97/06730 | 2/1997 |
| WO | WO 99/56821 | 11/1999 |
| WO | WO 99/66838 | 12/1999 |
| WO | WO 00/07494 | 2/2000 |
| WO | WO 01/54581 | 8/2001 |
| WO | WO 02/02008 | 1/2002 |
| WO | WO 02/32304 | 4/2002 |
| WO | WO 03/028804 | 4/2003 |
| WO | WO 03/037430 | 5/2003 |
| WO | WO 03/072025 A2 | 9/2003 |
| WO | WO 2003/090821 | 11/2003 |
| WO | WO 03/105687 | 12/2003 |
| WO | WO 2004/036372 | 4/2004 |
| WO | WO 2004/036377 | 4/2004 |
| WO | WO 2004/037114 | 5/2004 |
| WO | WO 2004/041080 | 5/2004 |
| WO | WO 2004/041351 | 5/2004 |
| WO | WO 2004/041352 | 5/2004 |
| WO | WO 2004-041353 | 5/2004 |
| WO | WO 2004/041359 | 5/2004 |

OTHER PUBLICATIONS

Notification of Transmittal of the International Search Report and the Written Opinion dated Apr. 13, 2005, International Application No. PCT/US2004/029851.

Navarro et al., "Evaluation of thermal and pain sensitivity in type I diabetic patients," Journal of Neurology, Neurosurgery, and Psychiatry, vol. 54, pp. 60-64, 1991.

Jamal, et al., "An improved automated method for the measurement of thermal thresholds. 1. normal subjects," Journal of Neurology, Neurosurgery, and Psychiatry, vol. 48, pp. 354-360, 1985

Fowler, et al., "A portable suystem for measuring cutaneous thresholds for warming and cooling," Journal of Neurology, Neurosurgery, and Psychiatry, vol. 50, pp. 1211-1215, 1987.

Yarnitsky et al., "Studies of heat pain sensation in man: perception thresholds, rate of stimulus rise and reaction time," Pain, vol. 40, pp. 85-91, 1990.

Fruhstorfer et al., "Method for quantitative estimation of thermal thresholds in patients," Journal of Neurology, Neurosurgery, and Psychiatry, vol. 39, pp. 1071-1075, 1976.

Arezzo et al., "Device for Quantitative Assessment of Thermal Sense in Diabetic Neuropathy," Diabetes, vol. 35, pp. 590-592, 1986.

Campbell et al., "Local Analgesia From Percutaneous Electrical Stimulation," Arch Neurol, vol. 28, pp. 347-350, 1973.

Kemler et al., "Spinal Cord Stimulation in Patients with Chronic Reflex Sympathetic Dystrophy," New Engl J Med, vol. 343, No. 9, pp. 618-624, 2000.

Kemler et al., "Impact of Spinal Cord Stimulation on Sensory Characteristics in Complex Regional Pain Syndrome Type I," Anesthesiology, vol. 95, pp. 72-80, 2001.

Larson et al., "Neurophysiological effects of dorsal column stimulation in man and monkey," J. Neurosurg., vol. 41, pp. 217-223, 1974.

Li, et al., "Windup leads to characteristics of central sensitization," Pain, vol. 79, pp. 75-82, 1999.

Mersket et al., "Classification of chronic pain: Descriptions of chronic pain syndromes and definitions of pain terms," IASP Press, Seattle, pp. 40-42, 1994.

Ochoa, "The human sensory unit and pain: New concepts, syndromes, and tests," Muscle & Nerve, vol. 16, pp. 1009-1016, 1993.

Ochoa et al., "Mechanical Hyperalgesias in Neuropathic Pain Patients: Dynamic and Static Subtypes," Ann Neurol., vol. 33, pp. 465-472, 1993.

Price, "The use of experimental pain in evaluating the effects of dorsal column stimulation on clinical pain," Pain, vol. 45, pp. 225-226, 1991.

Price et al., "Spatial and temporal transformations of input to spinothalamic tract neurons and their relation to somatic sensation", J Neurophysiol, vol. 41, pp. 933-947, 1978.

Raj et al., "Painless eletroiagnostic current perception threshold and pain tolerance threshold values in CRPS subjects and healthy controls: a multicenter study," Pain Practice, vol. 1(1), pp. 53-60, 2001.

Verdugo et al., "Quantitative Somatosensory Thermotest," Brain, vol. 115, pp. 893-913, 1992.

Yarnitsky et al., "Thermal testing: Normative data and repeatability for various test algorithms," J. Neurol Sci, vol. 125, No. 1, pp. 39-45, 1994.

Alo, et al., "Effects Of Spinal Cord Stimulation On Sensory Nerve Conduction Threshold Functional Measures", Neuromodulation, vol. 3, No. 3, pp. 145-154, 2000.

Mironer et al., "Pain Tolerance Threshold: A Pilot Study Of An Objective Measurement Of Spinal Cord Stimulator Trial Results", Pain Medicine, vol. 1, No. 2, pp. 110-115, 2000.

Lindblom et al., "Influence On Touch, Vibration And Cutaneous Pain Of Doral Column Stimulation Of Man," Pain, vol. 1, pp. 257-270, 1975.

Hord et al., "The predictive value of sympathetic block for the success of spinal cord stimulation", Neurosurgery, 53(3):626-32; discussion 632-3, 2003.

Shy et al., "Quantitative Sensory Testing," American Academy of Neurology, pp. 898-904 (2003).

Sindou et al., "Predictive Value of Somatosensory Evoked Potentials for Long-Lasting Pain Relief After Spinal Cord Stimulation: Practical Use for Patient Selection," Neurosurgery, vol. 52, No. 6, pp. 1374-1384 (2003).

Abe et al., "Change of Current Perception Threshold by Spinal Cord Stimulation,"Poster Presentation at the Annual Meeting of the Japanese Society of Pain Clinicians, Sendai, Japan, p. 1 (2003).

Samuelsson et al., "Thermal Quantitative Sensory Testing in Lumbar Disc Herniation," Eur Spine J., 11, pp. 71-75 (2002).

Rasche et al., "Quantitative Sensory Testing in Patients with Chronic Unilateral Radicular Neuropathic Pain and Active Spinal and Active Spinal Cord Stimulation," Neuromodulation, vol. 9, No. 3, pp. 239-247 (2006).

* cited by examiner

PATIENT SENSORY RESPONSE EVALUATION FOR NEUROMODULATION EFFICACY RATING

This application claims the benefit of U.S. provisional application No. 60/508,318, filed Oct. 2, 2003, and U.S. provisional application No. 60/508,354, filed Oct. 3, 2003, the entire content of each of which is incorporated herein by reference.

TECHNICAL FIELD

The invention relates to neuromodulation therapy and, more particularly, to techniques for determining and rating neuromodulation efficacy to aid in selection of neuromodulation programs.

BACKGROUND

Implantable medical devices are used to deliver neuromodulation therapy to patients to treat a variety of symptoms or conditions such as chronic pain, tremor, Parkinson's disease, epilepsy, incontinence, or gastroparesis. Neuromodulation may involve delivery of neurostimulation therapy, in the form of electrical pulses, via one or more leads that include electrodes located proximate to the brain, spinal cord, peripheral nerves, skin, neuronal ganglia, or nerves to organs. Neuromodulation may also involve use of an implantable drug delivery device, to chronically deliver metered dosages of a drug to target regions in the body via a catheter. Neuromodulation may involve the simultaneous use of both modalities, i.e., neurostimulation and drug delivery, for optimal efficacy.

Prior to implantation of a neuromodulation device, the patient may engage in a trial neuromodulation period, in which the patient receives an implanted or external trial neuromodulation device on a temporary basis. An external trial neurostimulator screener, for example, may be coupled to an implanted lead via a percutaneous lead extension. In either case, the trial neuromodulation permits a clinician to observe neuromodulation efficacy and determine whether implantation of a chronic neuromodulation device is advisable.

The trial neuromodulation period also may assist the clinician in selecting values for a number of programmable parameters in order to define the neuromodulation therapy to be delivered to a patient. For example, for a neurostimulation, the clinician may select an amplitude, which may be current- or voltage-controlled, and pulse width for a stimulation waveform to be delivered to the patient, as well as a rate at which the pulses are to be delivered to the patient. In addition, the clinician also selects particular electrodes within an electrode set on a lead to be used to deliver the pulses, and the polarities of the selected electrodes. With drug delivery, the clinician may select dosing and concentration of the drug in the device, and timing intervals also.

The results of the trial neuromodulation process can be inconsistent. For example, the trial neuromodulation process may be hampered by subjective and possibly inconsistent feedback from the patient concerning observed efficacy. In addition, the trial neuromodulation process may yield information that is indicative of short-term, diagnostic efficacy, but less indicative of long-term, prognostic success.

SUMMARY

In general, the invention is directed to techniques for determining and rating neuromodulation efficacy based on evaluation of the response of the patient to external sensory stimuli at different times. In particular, the patient response is evaluated before intervention by delivery of neuromodulation therapy, such as neurostimulation, and then during delivery of neuromodulation therapy to detect changes in the patient sensory response.

Evaluation of changes in patient sensory response caused by neuromodulation can provide a prediction of efficacy of neuromodulation in general, including electrical neurostimulation and drug delivery. Hence, the invention may provide a clinician with not only a diagnostic tool in determining short term, clinical results obtained from neurostimulation, but also a prognostic tool in predicting the likely efficacy of a chronically implanted neurostimulator or chronically implanted drug delivery device over a longer period of time. In other words, the invention may support evaluation of both diagnostic, i.e., short term, efficacy, and prognostic, i.e., long term, efficacy.

In addition, the invention may provide a system capable of delivering sensory stimuli on a quantitative basis in a manner coordinated with delivery of neuromodulation therapy. A neuromodulation device programmer may provide a platform for controlling delivery of the sensory stimuli, delivery of neuromodulation therapy, and generation of useful rating information about neuromodulation efficacy based on patient sensory response to the stimuli. In operation, the programmer controls application of selected sensory stimuli to the patient's body and records the patient's verbal or physiological responses to the stimuli.

The invention may support delivery of different types of sensory stimuli, e.g., electrical and vibratory stimuli, and evaluation of neuromodulation efficacy based on patient response to the different sensory stimuli types before and during delivery of neurostimulation therapy. Other sensory stimuli include tactile, thermal, pressure and chemical stimuli. For example, the effect of neurostimulation therapy on sensory perception thresholds, sensory tolerance limits and the like for different types of stimuli may be evaluated to determine short-term efficacy of neuromodulation. Moreover, the effect of neurostimulation therapy on patient response to some types of sensory stimuli may be prognostic for long-term success of the neuromodulation therapy. In each case, consideration of the patient's responses to different types of stimuli may provide a reliable correlation that promotes selectivity and specificity.

In one embodiment, the invention provides a method comprising applying a first type of external sensory stimulation to a patient, obtaining a baseline measurement of patient sensory response to the first type of external sensory stimulation, applying a second type of external sensory stimulation to a patient, and obtaining a baseline measurement of patient sensory response to the second type of external sensory stimulation. The method further comprises applying neuromodulation therapy to the patient simultaneously with application of the first type of external sensory stimulation, obtaining a test measurement of patient sensory response to the first type of external sensory stimulation during simultaneous application of the first type of external sensory stimulation and the neuromodulation therapy, applying neuromodulation therapy to the patient simultaneously with application of the second type of external sensory stimulation, obtaining a test measurement of patient sensory response to the second type of external sensory stimulation during simultaneous application of the second type of external sensory stimulation and the neuromodulation therapy, and evaluating efficacy of the neuromodulation therapy based on a comparison of the baseline measurements and the test measurements.

In another embodiment, the invention provides a system comprising a first sensory stimulation unit to apply a first type of external sensory stimulation to a patient, and a second sensory stimulation unit to apply a second type of external sensory stimulation to the patient, a neuromodulation unit to apply neuromodulation therapy to the patient. The system further comprises a device to obtain a baseline measurement of patient sensory response to the first type of external sensory stimulation without application of the neuromodulation therapy, obtain a baseline measurement of patient sensory response to the second type of external sensory stimulation without application of the neuromodulation therapy, obtain a test measurement of patient sensory response to simultaneous application of the first type of external sensory stimulation and the neuromodulation therapy, and obtain a test measurement of patient sensory response to simultaneous application of the second type of external sensory stimulation and the neuromodulation therapy. The device evaluates efficacy of the neuromodulation therapy based on a comparison of the baseline measurements and the test measurements.

In an added embodiment, the invention provides a method comprising applying external sensory stimulation to a patient, wherein the external sensory stimulation includes at least one of tactile, vibrational, thermal, pressure, chemical stimulation. The method further comprises obtaining a baseline measurement of patient sensory response to the external sensory stimulation, applying neuromodulation therapy to the patient simultaneously with application of the external sensory stimulation, obtaining a test measurement of patient sensory response to the external sensory stimulation during simultaneous application of the external sensory stimulation and the neuromodulation therapy, and evaluating efficacy of the neuromodulation therapy based on a comparison of the baseline measurements and the test measurements.

In a further embodiment, the invention provides a system comprising a sensory stimulation unit to apply external sensory stimulation to a patient, wherein the external sensory stimulation includes at least one of tactile, vibrational, thermal, pressure, chemical stimulation, and a neuromodulation unit to apply neuromodulation therapy to the patient. A device obtains a baseline measurement of patient sensory response to the external sensory stimulation without application of the neuromodulation therapy, obtains a test measurement of patient sensory response to simultaneous application of the external sensory stimulation and the neuromodulation therapy, and evaluates efficacy of the neuromodulation therapy based on a comparison of the baseline measurements and the test measurements.

According to an added embodiment, changes in patient sensory response may be evaluated for a second external sensory stimulus only if the changes in patient sensory response for a first external sensor stimulus do not indicate a sufficiently large change, creating ambiguity. On the other hand, if the first measurements are sufficiently large, the second measurements can be avoided. In particular, according to this approach, baseline vibration measurements are obtained during application of a first type of stimulation, e.g., vibratory stimulation, to the patient.

Then, baseline measurements may be obtained for a second type of stimulation, e.g., electrical stimulation. Upon activation of a neurostimulation program, similar "test" measurements are obtained for the vibration, and the baseline and neurostimulation "test" vibration measurements are compared. The "test" measurement refers to the measurement obtained during simultaneous activation of the neurostimulation program, and the external sensory stimulation.

If the comparison between the baseline measurement and the test measurement is not favorable to the point of being definitive, then electrical measurements may be taken for patient sensory response to external electrical stimulation: If the vibratory comparison is definitive, however, the clinician or patient may simply forego the electrical test measurement and conclude that the applicable neurostimulation program is not likely to be efficacious.

Baseline measurements may be done at any time either before application of the neuromodulation therapy, or by turning off the neuromodulation therapy, and waiting for a sufficient period of time so that the effects of neuromodulation therapy have substantially diminished, typically between two and 48 hours.

As a variation, the process may take the baseline electrical measurement and neurostimulation test electrical measurement only if the vibratory measurements are equivocal, i.e., not definitive. In this case, the vibratory stimulus serves as a primary threshold test. In another embodiment, if a patient's visual analog scale (VAS) score rises with neuromodulation, then the process can be terminated without testing other measurements such as electrical or vibratory external sensory stimulation.

In some embodiments, the neuromodulation used in evaluating changes in patient sensory response may be delivered by a trial neurostimulator via an implanted lead and a percutaneous lead extension. Alternatively, the trial neurostimulator may be an implanted neurostimulation device. In other embodiments, however, the neurostimulation may be delivered by a transcutaneous electrical neurostimulation (TENS) device. Advantageously, the use of a TENS device would not require any surgery or non-surgical implantations of leads. Instead, electrodes associated with the TENS device may be attached to the skin of the patient. As a further alternative, neuromodulation may be delivered by application of a drug to a patient orally, by injection, by implantable drug pump, by external drug pump, by transdermal patch or other delivery mechanisms.

The invention may provide a number of advantages. For example, the invention may allow a clinician to better judge the likely efficacy of neuromodulation therapy for a patient, on both a short-term and long-term basis. In this manner, the clinician may be better equipped to make decisions about whether to implant a neuromodulation device on a chronic basis.

For example, the invention may be useful in diagnosing features of the patient's physiological sensory state, and providing prognostic information about the long-term efficacy of neuromodulation therapy for the patient. The result may provide greater certainty in the selection of candidates for neuromodulation therapy, especially when patient sensory results are correlated for different types of sensory stimuli to provide greater selectively and specificity.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
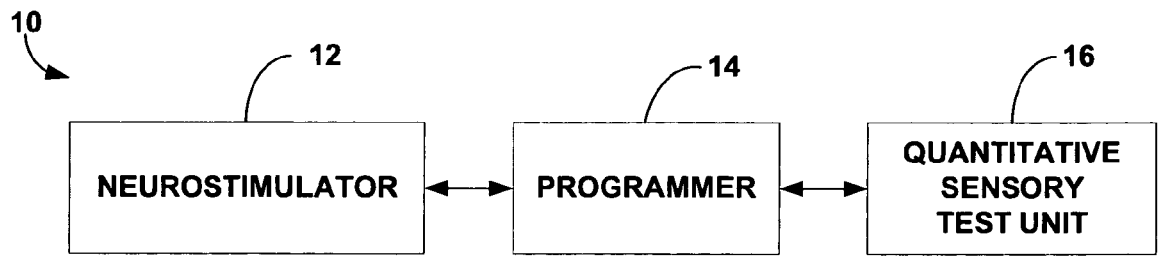
FIG. 1 is a block diagram illustrating a system for evaluating patient sensory response to rate neuromodulation efficacy.

FIG. 1 is a block diagram illustrating a system 10 for evaluating patient sensory response to rate neuromodulation efficacy, such as efficacy of neurostimulation or drug delivery. As shown in FIG. 1, system 10 includes a neurostimulator 12, a programmer 14 and a quantitative sensory test (QST) unit 16. System 10 implements a technique for rating neuromodulation efficacy based on evaluation of the response of the patient to external sensory stimuli, such as electrical, vibratory, tactile, thermal, pressure or chemical stimulation before and during delivery of neurostimulation therapy.

External chemical sensory stimulation may involve delivery of a drug to the patient to elicit a sensory response, e.g., capsaicin topically applied to the skin to excite unmyelinated fibers or nitric oxide donors to cause vasodilation, or to temporarily change the patient's pain symptoms, e.g., an intraspinal dose of clonidine or phentolamine to suppress the sympathetic system, or an intraspinal dose of an NMDA blocker such as Ketamine.

System 10 delivers external sensory stimuli on a quantitative basis in a coordinated manner with delivery of neurostimulation therapy, and generates rating information for neuromodulation efficacy based on patient sensory response to the stimuli. The efficacy rating may pertain not only to the efficacy of neurostimulation but also drug delivery if a sufficient correlation between efficacy of both types of neuromodulation has been made. In operation, programmer 14 controls neurostimulator 12 to delivery neurostimulation therapy to a patient, and controls QST unit 16 to apply selected external sensory stimuli to the patient's body. Programmer 14 records the patient's report, including verbal or physiological responses to the stimuli, as indicated by the clinician or the patient.

System 10 may support delivery of different types of sensory stimuli, e.g., electrical and vibratory stimuli, and evaluation of neuromodulation efficacy based on patient sensory response to the different stimuli types. For example, the effect of neurostimulation therapy on sensory perception thresholds, pain perception thresholds, pain tolerance limits and the like for different types of stimuli may be measured and evaluated to determine short-term efficacy of neurostimulation, and possibly drug delivery.

Hence, even if the evaluation process makes use of electrical neurostimulation, the efficacy rating may also apply to drug delivery as another form of neuromodulation. Drug delivery for neuromodulation may include delivery of a drug to a patient orally, by injection, by implantable drug pump, by external drug pump, by transdermal patch or other delivery mechanisms. Regardless of the type of sensory measurement performed, system 10 is used to make a comparison of the applicable measurements, with and without application of neuromodulation. In this manner, system 10 may be used to evaluate the effect of neuromodulation therapy on patient response to some types of sensory stimuli, providing an indication of short-term (diagnostic) and long-term (prognostic) success of the neuromodulation therapy.

In each case, system 10 may consider patient sensory response to multiple types of external sensory stimuli, and also patient subjective response to the neuromodulation therapy or its side effects, to provide a correlation that promotes selectivity, sensitivity and specificity. Hence, the patient may provide reports in terms of subjective input concerning perceived efficacy, such as perceived pain relief and coverage area, as will be described in greater detail below.

System 10 may be used in the clinic, or even at home by the patient in some embodiments, to test various parameters of neurostimulation, including polarities of electrodes, to determine which one best changes the patient sensory response to the QST-based external sensory stimulation. If system 10 is used at home, QST stimulation activation and settings may be blinded to the patient, or they may be given to the patient when the tests are done, for the patient to look up the interpretation, and adjust the therapy.

Neurostimulator 12 may include an implanted or external pulse generator and one or more implanted leads with electrodes to deliver neurostimulation energy to a patient. For external applications, neurostimulator 12 may be coupled to one or more implanted leads via a percutaneous lead extension for a trial of several days or weeks. In other embodiments, neurostimulator 12 may be temporarily implanted within the patient and coupled to one or more implanted leads via an implanted lead extension. Neurostimulator 12 may be a trial neurostimulator, often called a screener, that is used to evaluate possible implantation of a chronic neurostimulator in a patient.

A clinician contemplating implantation of a neurostimulation device or drug delivery device to treat patients may consider the patient's history, symptoms, and prior therapies or therapy failures as a way to predict efficacy of neurostimulation therapies. In addition, the clinician may rely on trial neurostimulation. Trial neurostimulation may involve placement of a trial lead to screen the patient at home for a short period of time, such as a week, to determine if the therapy is effective in relieving the symptoms.

When the patient returns to the clinic, he is asked about his experiences. In addition, the patient may use a patient report of pain relief such as a visual analog scale (VAS), report of percent pain relief, word choice lists, validated pain and activities questionnaires, or other techniques, to quantify and qualify the efficacy of the treatment. In some embodiments, system 10 may make use of a combination of tests and stimulation parameters, which the patient uses at home during the testing phase, and results from a particular trial may be used, automatically or with patient cooperation, to direct the next trial.

In accordance with the invention, the patient also undergoes QST-based external sensory stimulation in the clinic to assess the effects of the neurostimulation therapy in altering patient sensory response. If the patient's sensory response, alone or in combination with the neuromodulation efficacy observed during the trial, indicates likelihood of successful therapy, a decision to replace neurostimulator 12 with a chronic, implantable neurostimulator or drug delivery device can be made by the clinician with heightened confidence.

In particular, the patient may have a placebo response, and these tests can be used to correlate changes in physiological responses to stimuli due to the therapy to the subjective feedback. With experience and research, the sensitivity and specificity of the algorithm used may be so great that it is more reliable than the patient's oral feedback, and the medical profession may prefer to use it, or to extend a trial if there is a discrepancy between a patient's oral feedback and the sensory measurements.

Neurostimulator 12 delivers neurostimulation therapy to the patient according to one or more neurostimulation therapy programs. A neurostimulation therapy program may include values for a number of parameters, and the parameter values define the neurostimulation therapy delivered according to that program. In embodiments where neurostimulator 12 delivers neurostimulation therapy in the form of electrical pulses, the parameters may include voltage- or current-controlled pulse amplitudes, pulse widths, pulse rates, and the like. In embodiments where drugs are delivered, parameters may include dosage and timing, or even the use of placebos.

Further, the parameters for a program may include information identifying which electrodes have been selected for delivery of pulses according to the program, and the polarities of the selected electrodes. If the patient is being evaluated for an implantable drug delivery device, rather than an implantable neurostimulator, a single external sensory test program or small set of programs found to be prognostic as to drug delivery efficacy may be selected. If the patient is being evaluated for an implantable neurostimulator, however, evaluation of different programs may aid not only in determining whether to implant a neurostimulator, but also in identifying specific programs that may be efficacious.

For example, the trial neurostimulation period also may assist the clinician in selecting values for a number of programmable parameters in order to define the neurostimulation therapy to be delivered to a patient. For example, the clinician may select an amplitude, which may be current- or voltage-controlled, and pulse width for a stimulation waveform to be delivered to the patient, as well as a rate or frequency at which the pulses are to be delivered to the patient. In addition, the clinician also selects particular electrodes within an electrode set carried by an implanted lead to be used to deliver the pulses, and the polarities of the selected electrodes.

QST unit 16 may comprise any of a variety of devices capable of applying sensory stimuli to the patient. For example, the stimuli may take the form of electrical stimulation, vibratory stimulation, thermal stimulation, tactile stimulation, or a combination of two or more of the foregoing types of stimulation. The sensory stimulation may be applied without neurostimulation to obtain baseline sensory measurements, and then with neurostimulation during the therapy trial in order to obtain test measurements and identify changes that reveal the effect of neurostimulation on the patient's sensory processes. In some embodiments, QST unit 16 may also deliver sensory stimulation by delivery of a drug to the skin (external) or intraspinally (internal) to cause a change in the patient's pain symptoms, or to cause a controlled degree of pain or affect the autonomic nervous system.

In an exemplary embodiment, QST unit 16 may generate both electrical and vibratory stimulation, although not necessarily at the same time. Consideration of the patient's recorded responses to multiple types of sensory stimuli may provide a correlative relationship that promotes selectivity and specificity in evaluating neuromodulation therapy. Commercially available devices may be used, e.g., the NervScan™ LLC device of Neurotron, Inc., or the VSA-3000 Vibratory Sensory Analyzer of Medoc, Inc., or even any of the commercially available TENS (transcutaneous electrical nerve stimulation) devices, which use cutaneous electrodes.

In some embodiments, programmer 14 serves as a platform to control operation of both neurostimulator 12 and QST unit 16, e.g., in a coordinated manner. In addition, programmer 14 may provide features to support evaluation of a patient's responses to sensory stimuli applied by QST unit 16, and thereby judge the efficacy of the neurostimulation therapy applied by neurostimulator 12. In other embodiments, neurostimulator 12 and QST unit 16 may be controlled separately, e.g., by a neurostimulation programmer in the case of neurostimulator 12 and by an integrated control unit in the case of QST unit 16. Alternatively, programmer 14 and QST unit 16 may be integrated with one another for clinician convenience, into the trial therapy screening device, or even into the fully implanted neurostimulation device. As will be described, in each case, system 10 provides features to carry out neurostimulation, application of external sensory stimulation, and recording and evaluation of patient sensory response.

A clinician may use programmer 14 to not only program trial neurostimulation therapy delivered by neurostimulator 12 for the patient, but also select neurostimulation therapy programs for an implanted neurostimulator if implantation is elected following the trial period. In particular, the clinician may use programmer 14 to create neurostimulation therapy programs based on efficacy, including symptom relief, coverage area relative to symptom area, and side effects, as well as observed effects of the neurostimulation programs on patient sensory response to the QST stimuli. In particular, as will be described, effects of the neurostimulation program in modifying patient sensory response to particular external sensory stimuli applied by QST unit 16 may provide a reliable indication of short-term efficacy and long-term neurostimulation success.

In another embodiment, during trial neurostimulation, components of the therapy delivering device are not implanted in the patient, nor are there percutaneous extensions. Rather, a TENS (transcutaneous electrical nerve stimulation) device is used as neurostimulator 12. The TENS unit may produce therapeutic benefit on its own, and hence feel and perform much like an implanted neurostimulation screening device. Alternatively, it may cause changes in processing of sensory information very similar to those of implanted neurostimulation devices, which can be fully explored using the QST unit 16.

Figure 2:
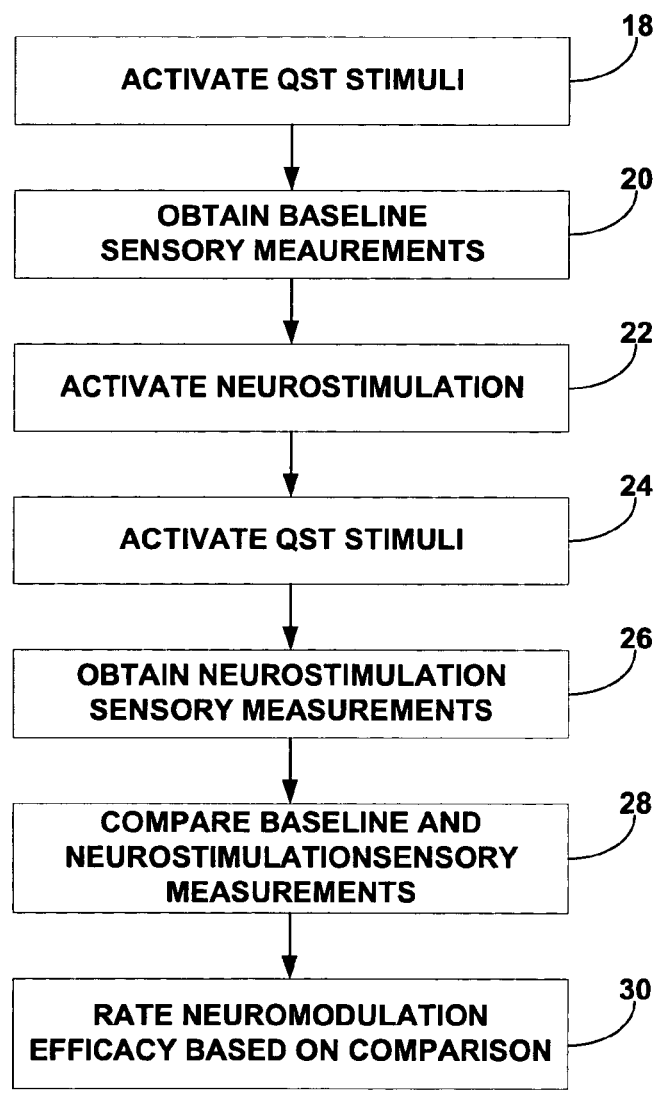
FIG. 2 is a flow diagram illustrating a technique for evaluating patient sensory response to rate neuromodulation efficacy.

FIG. 2 is a flow diagram illustrating a process for evaluating patient sensory response to rate neuromodulation efficacy, such as implanted neurostimulation device efficacy or implanted drug delivery device efficacy. As shown in FIG. 1, the process involves activating QST unit 16 to deliver QST stimuli (18) such that external sensory stimulation is applied to a patient. The external sensory stimulation may be applied in a series of controlled amplitude or frequency steps to obtain sensory response information such as perception thresholds, pain thresholds, pain tolerance limits or other sensory information. Upon obtaining baseline sensory response measurements from the patient (20), which may be recorded by programmer 14, neurostimulator 12 activates delivery of neurostimulation therapy to the patient (22). In conjunction with delivery of neurostimulation by neurostimulator 12, QST unit 16 delivers QST stimuli to the patient (24).

Programmer 14 obtains patient neurostimulation sensory "test" measurements (26) in order to assess any change in sensory response of the patient to the QST stimuli during the application of neurostimulation. The sensory measurements obtained during application of neurostimulation therapy will be referred to herein as neurostimulation sensory measurements or "test" measurements to distinguish those measurements from the baseline sensory measurements obtained when neurostimulation therapy is not applied. Programmer 14 compares the baseline and neurostimulation sensory test measurements (28), and then rates the efficacy of neuromodulation based on the comparison (30).

The neuromodulation efficacy may be rated in terms of both short-term efficacy and likelihood of long-term success. A wide variety of measurements may be made, and additional measurements may be derived, to contribute to the efficacy rating, such as the patient's subjective reports on the amount of pain relief, e.g., percent relief, visual analog scale, or word choice, responses to lists of words describing their condition or satisfaction, responses recorded in validated measurement instruments and questionnaires, e.g., Oswestry Inventory, SF-36 Inventory, or Sickness Impact Profile.

Figure 3:
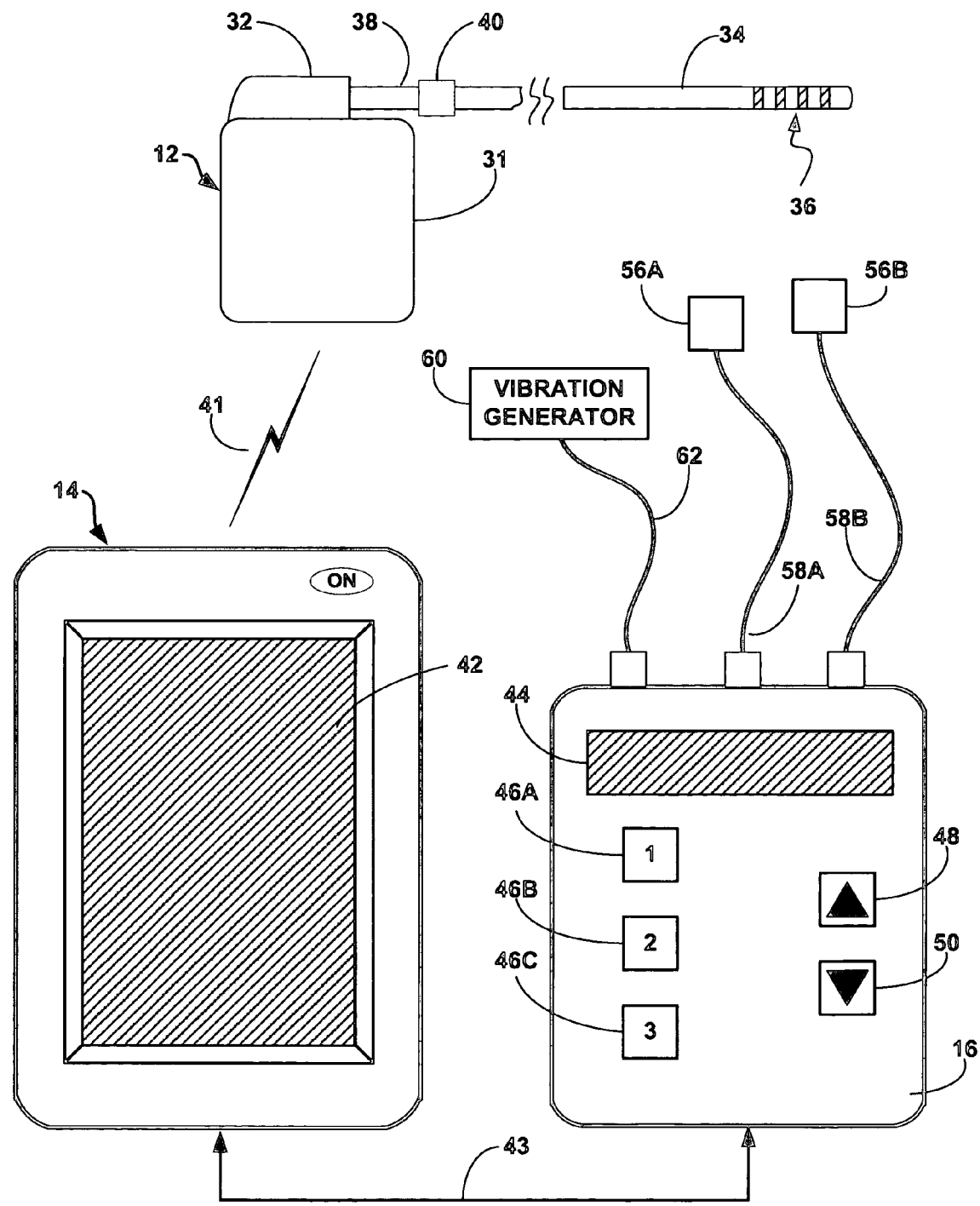
FIG. 3 is a conceptual diagram illustrating the system of FIG. 1 in greater detail.

FIG. 3 is a conceptual diagram illustrating the system 10 of FIG. 1 in greater detail. As shown in FIG. 3, neurostimulator 12 may include a housing 31 with a connector block 32 to attach to a lead 34. Lead 34 is implantable and includes a plurality of ring electrodes 36 disposed adjacent a distal tip of the lead. A lead extension 38 and coupler 40 receive lead 34, and couple the lead to connector block 32 for connection to pulse generator electronics within neurostimulator 12. In some embodiments, housing 31 is designed for temporary implantation within the patient. In other embodiments, housing 31 may be external to the patient. In this case, lead extension 38 may be a percutaneous lead extension.

Electrodes 36 are located proximate an appropriate stimulation site, e.g., along the spine for spinal cord stimulation (SCS) to reduce pain experienced by the patient. However, the invention is not limited to the configuration of leads 16 shown in FIG. 1 or the delivery of SCS therapy. For example, one or more leads 16 may extend from neurostimulator 12 to the brain (not shown) of the patient, and neurostimulator 12 may deliver deep brain stimulation (DBS) therapy to patient to treat, for example, tremor or epilepsy. As further examples, one or more leads 16 may be implanted proximate to the pelvic nerves (not shown) or stomach (not shown), and neurostimulator 12 may deliver neurostimulation therapy to treat incontinence, gastroparesis, or sexual dysfunction. The form of the QST stimuli may vary in modality, or the site of the application of the QST stimuli may vary appropriately for each of these therapies.

In the example of FIG. 3, programmer 14 may take the form of a handheld or desktop computing device with a user interface such as a touchscreen 42. Touchscreen 42 serves as a user interface to permit a clinician to view information presented by programmer 14, and enter information to control application of neurostimulation therapy, including programming of parameters within neurostimulator 12, e.g., via a wired or wireless connection 41. In some embodiments, programmer 14 may include a keypad and pointing device that permit a user to interact with the programmer.

In other embodiments, as depicted in FIG. 3, a touchscreen 42 permits the user to input information, e.g., using a stylus. Programmer 14 may accept information from the clinician to control application of external sensory stimulation by QST unit 16, e.g., via a wired or wireless connection 43. Upon application of neurostimulation therapy and external sensory stimulation, the clinician may enter information concerning the patient's sensory responses and other efficacy-related information, via touchscreen 42. Touchscreen 42 is depicted in FIG. 3 for purposes of example, and programmer 14 is in no way limited to a particular type of user interface.

With further reference to FIG. 3, QST unit 16 includes a display screen 44 to present status information concerning external sensory stimulation applied to a patient by the QST unit. The status information may be coded, especially as regards intensity of the applied stimulus. Also, in the example of FIG. 3, QST unit 16 may include various input buttons 46A–46C (hereinafter buttons 46), or other controls, to select different types, levels or programs for delivery of external sensory stimulation. In addition, QST unit 16 may include input media, such as up/down buttons, 48, 50, for increasing or decreasing stimulation levels, or stepping through different options. Other types of input media may be used, such as analog controls, touchscreens, switches, sliders, and the like. As an alternative, or in addition, the functionality of buttons 46, 48, 50 may be determined by similar input media presented by programmer 14.

In the example of FIG. 3, QST unit 16 is capable of delivering several modes of sensory stimuli. For example, QST unit 16 may apply electrical current to a patient via electrodes 56A, 56B, which are coupled to the QST unit via leads 58A, 58B, respectively. Electrodes 56 may be surface electrodes that can be adhesively attached to the skin at a desired location on the patient's body. Current travels between electrodes 56 to stimulate the patient's tissue. Also, QST unit 16 may be coupled to drive a vibration generator 60 via a lead 62. Vibration generator 60 may be configured to attach to or be placed upon a portion of the patient's body to deliver vibratory energy to the patient. In each case, QST unit 16 controls parameters associated with delivery of the external sensory stimulation, such as level, frequency, duration and the like.

Electrodes 56 and vibration generator 60, or other sources of sensory stimulation, may be placed on the patient's skin at a position desired by the clinician. In some cases, it may be desirable to place electrodes 56 and vibration generator 60 in a region implicated by a particular symptom. If the patient suffers from complex regional pain syndrome (CRPS), for example, it may be desirable to apply the external sensory stimulation in the region in which pain and other symptoms appear to be focused. In other cases, it may be desirable to apply the external sensory stimulation at a point in or near a suspected propagation path from the patient's nervous system to the region of pain.

It is anticipated that application of the sensory stimuli could be optimally done in or along the same dermatome, thereby affecting the same spinal cord segment as the pain and as the neurostimulation site. If the neurostimulator 12 used for trial neurostimulation is a TENS device, then its skin electrodes might be placed in the middle of the skin area of worst pain, and the sensory stimuli could be delivered to the fingers or toes of that same dermatome. Alternatively, the external sensory stimulation may be applied in locations that are not associated with a region of pain to prevent discomfort.

Figure 4:
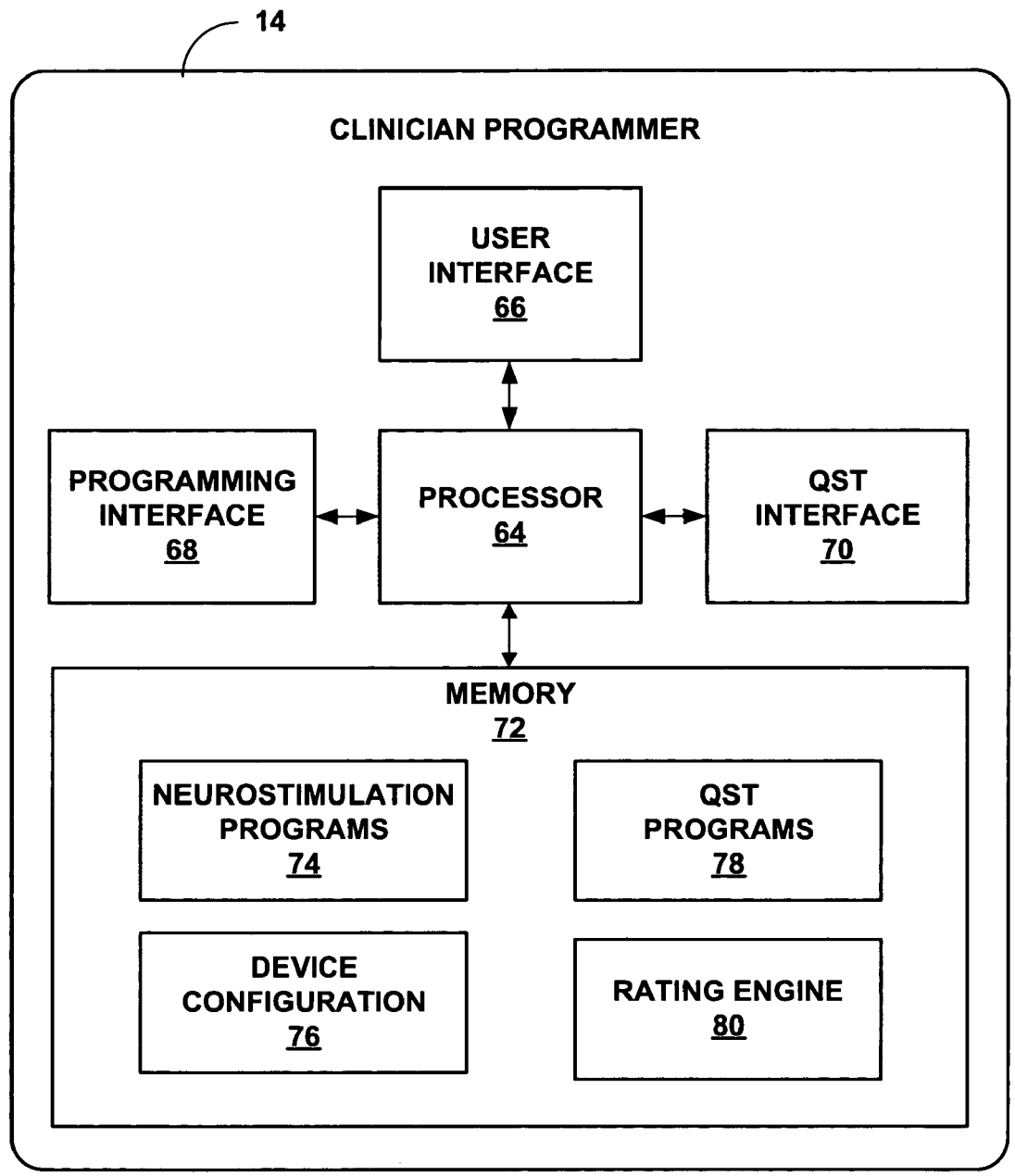
FIG. 4 is a block diagram illustrating a clinician programmer for use in the system of FIG. 1.

FIG. 4 is a block diagram illustrating a neurostimulation programmer for use in the system of FIG. 1. As shown in FIG. 4, clinician programmer 14 may include a processor 64, a user interface 66, a programming interface 68, a QST interface 70, and a memory 72. Processor 64 executes instructions stored in memory 72 to communicate with neurostimulator 12 via programming interface 68 and QST unit 16 via QST interface 70. In particular, processor 64 programs neurostimulator 12 to use different amplitudes, pulse widths, rates, and electrode configurations as specified by different neurostimulation programs 74 stored in memory 72. Memory 72 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

Processor 64 may select neurostimulation programs 74 based on a stored device configuration 76 that defines the configuration and capabilities of neurostimulator 12. Programming interface 68 may take the form of a wired or wireless communication medium. Processor 64 drives QST unit 16 via QST interface 70 to perform one or more QST programs 78 stored in memory. Processor 64 may include a microprocessor, a controller, a DSP, an ASIC, an FPGA, discrete logic circuitry, or the like. QST programs 78 may define different types of external sensory stimulation, different processes for application of external sensory stimulation, and combinations of different types of external sensory stimulation to be applied to the patient. QST interface 70 may take the form of a wired or wireless communication medium. In some embodiments, however, clinician programmer 14 may be integrated with QST unit 16 to form an integrated trial neurostimulation and neuromodulation efficacy rating system.

Processor 64 further executes a rating engine 80 to accept information from a user, e.g., via user interface 66, concerning the efficacy of neurostimulation therapies and the responses of the patient to external sensory stimulation both before and during application of neurostimulation. For example, rating engine 80 may accept information concerning the parameters associated with a particular neurostimulation program, the types and amounts of external sensory stimulation applied to a patient, and subjective responses of the patient.

Rating engine 80 may take into account baseline sensory measurements in the absence of neuromodulation and sensory "test" measurements taken during application of neuromodulation, and compare the measurements to determine the effect of the neuromodulation therapy. Changes in sensory or pain perception thresholds, pain tolerance limits and other changes may be considered in evaluating the effect of neuromodulation therapy. Rating engine 80 may also use non-sensory information in determining its output, such as patient selection of words from lists, patient information from past history, medications usage, patient evaluations on inventories (Oswestry, SF-36 and others) or even patient subjectively reported or explicitly recorded activity level.

Figure 5:
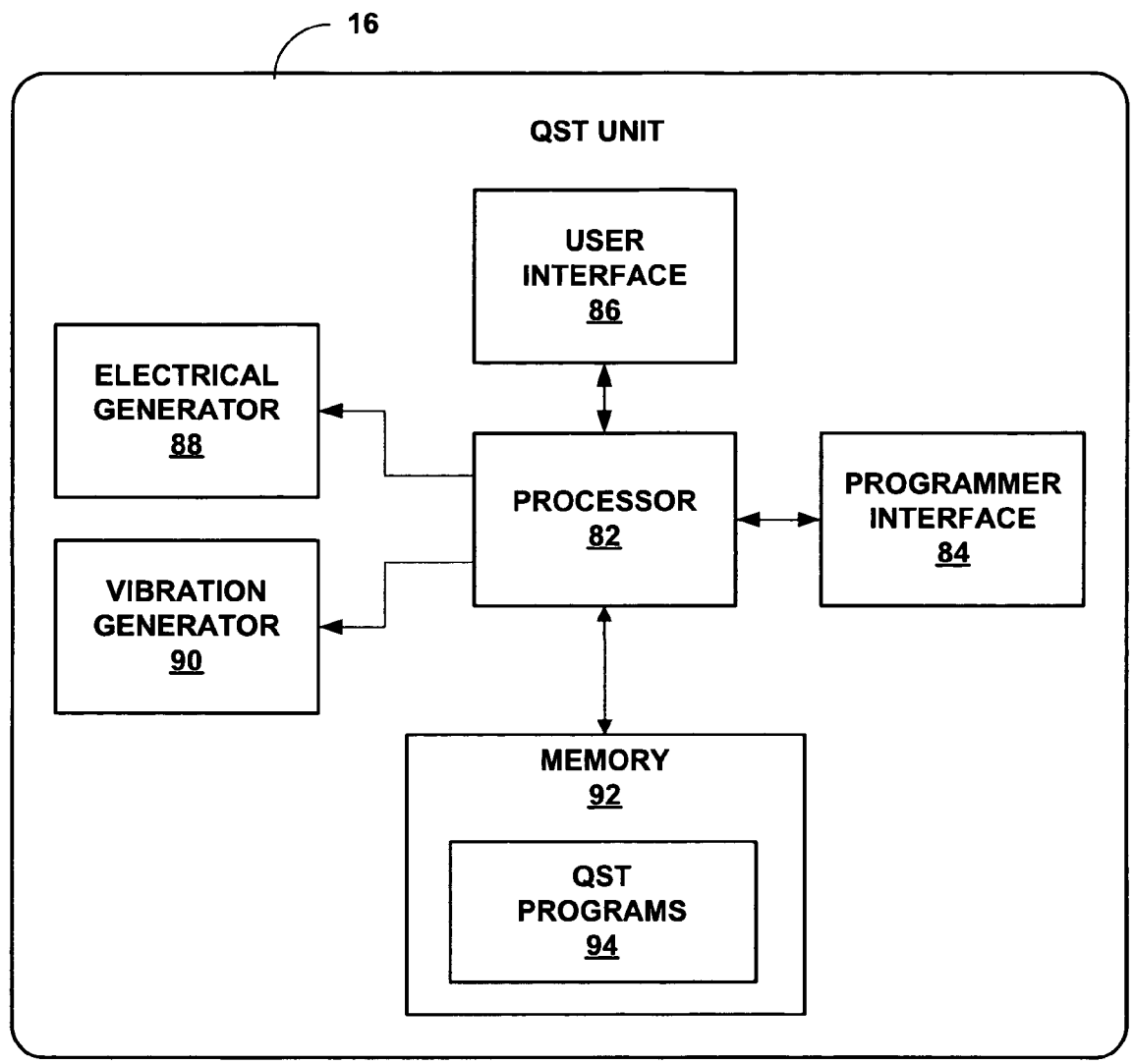
FIG. 5 is a block diagram illustrating a quantitative sensory test unit for use in the system of FIG. 1.

FIG. 5 is a block diagram illustrating a quantitative sensory test unit for use in the system of FIG. 1. As shown in FIG. 5, QST unit 16 includes a processor 82, a programmer interface 84, user interface 86, an electrical generator 88, a vibration generator 90, and a memory 92. Memory 92 stores one or more QST programs 94 that define parameters associated with delivery of external sensory stimulation, such as types, levels, and durations. Memory 92 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like. Programmer interface 84 communicates with QST interface 70 of clinician programmer 14. User interface 86 may correspond to display 44, and buttons 46, 48, 50 of FIG. 3.

Processor 82 controls the electrical generator 88 by providing parameters associated with delivery of electrical stimulation current between electrodes 56 via leads 58. Processor 82 may include a microprocessor, a controller, a DSP, an ASIC, an FPGA, discrete logic circuitry, or the like. Processor 82 also controls vibration generator 90 by providing parameters associated with delivery of vibratory energy to the patient. The control of electrical generator 88 and vibration generator 90 may follow parameters specified by QST programs 94. Although electrical and vibratory stimulation are depicted in FIG. 5 for purposes of illustration, additional or alternative types of external sensory stimulation may be provided by QST unit 16. However, delivery of both electrical and vibratory stimulation may yield aggregate patient sensory response data that is more specific and selective in indicating the likelihood of short-term and long-term success for an implantable neurostimulator.

In operation, processor 82 responds to input from a user or instructions communicated from clinician programmer 14 to selectively apply each type of external sensory stimulation to the patient. To obtain baseline sensory measurements, QST unit 16 may apply electrical stimulation in a series of steps with increasing amplitude or duration. In some embodiments, the electrical stimulation may be delivered as a sinusoidal waveform or other waveform stimulation pulses at various frequencies, including frequencies in the range of 5 to 250 Hz, and possibly higher, and at various amplitudes, which may be successively increased to capture a nonpainful perception threshold, followed by a pain perception threshold and then a pain tolerance limit.

For electrical stimulation, the pain tolerance limit may represent the maximum stimulation that a patient can withstand in terms of pain level. For example, the patient or the clinician may record the first step at which the patient can actually perceive the stimulation, and then also record the step at which the stimulation reaches the patient's pain tolerance ability. If the patient's sensory response changes with neurostimulation such that the patient can tolerate more QST pain, there may be a helpful correlation to the efficacy of neuromodulation in relieving pain symptoms suffered by the patient.

For vibratory stimulation, the perception threshold may represent the threshold for sensation of vibratory stimuli, without measuring a painful sensory response. This type of vibratory stimulation test could be performed several times during the course of trial neurostimulation in order to assess any changes. The vibratory stimulation may be accomplished with a voicecoil, piezoelectric, or other type of electromechanical transducer capable of generating vibration at selected frequencies and amplitudes. Again, patient sensory response to vibratory stimulation may be characterized in terms of perception thresholds, and possibly pain thresholds at higher amplitudes, e.g., a patient has dynamic mechanical allodynia. The perception threshold for vibration or light touch is usually a function of nerve fibers that have a large diameter (called A-beta fibers); while perception of pain is usually a function of nerve fibers with smaller diameters (A-delta, or C).

Other types of stimulation may include tactile stimulation in which a patient may be asked to resolve the presence of two or more tactile point sources based on varying distances between the point sources and varying contact force. Patient sensory response to tactile stimulation may be characterized in terms of the patient's ability to discriminate different tactile point sources, given a particular separation distance and contact force. Thermal stimulation may involve delivery of heat to the patient, i.e., thermal pulse trains or steady heat ramps. For thermal stimulation, patient sensory response can be characterized in terms of perception thresholds indicating the patient's first conscious sensation of heat or cold, and pain thresholds for first sensations that are described as painful heat or cold by the patient, and pain tolerance limits as the hottest or coldest pain that the patient could tolerate.

The patient may also give a subjective verbal report of the pain level with any particular thermal stimulus, by giving an oral analog scale, i.e., saying that on a scale of 0 (no pain) to 100 (worst possible pain), the pain at that instance was, e.g., "65." This sensory response information may be entered into QST unit 16 or clinician programmer 14. Similar baseline measurement information can be obtained for vibratory stimulation, as well as for other types of stimulation, if desired. In each case, the baseline measurements are obtained in the absence of neurostimulation. The measurements may be obtained in one session, different sessions, or over a series of sessions. For example, the measurements may be taken on a daily basis throughout the patient's usage of the trial neurostimulation therapy, or even with each time the patient changes the therapy in his own home.

Once the baseline measurements are obtained, the clinician activates neurostimulator 12 via clinician programmer 14 to apply neurostimulation therapy and thereby obtain test measurements in the presence of both neurostimulation and sensory stimulation. In particular, in addition to recording basic efficacy information, e.g., noting pain relief or other therapeutic effect as well as perceptible side effects, as subjectively observed by the patient, clinician programmer 14 may be used to record sensory measurements. Specifically, for each neurostimulation program applied to the patient, clinician programmer 14 or the clinician also may apply external sensory stimulation using QST unit 16. In this manner, the clinician can evaluate the effect of neurostimulation on patient sensory response to the external sensory stimulation.

Comparison of the baseline response measurements to the neurostimulation sensory test measurements may provide a reliable indication of short-term efficacy and long-term success of neurostimulation therapy. This indication can help the clinician make a more confident decision of whether to implant a neurostimulation device. In addition, the resulting comparison information can be formulated for different neurostimulation programs and analyzed by the rating engine implemented by clinician programmer 14 to identify the most effective neurostimulation programs. This can allow the clinician's staff or the patient to try numerous neurostimulation parameters, and rate the efficacy for each one, in a manner less subjective than current techniques.

Figure 6:
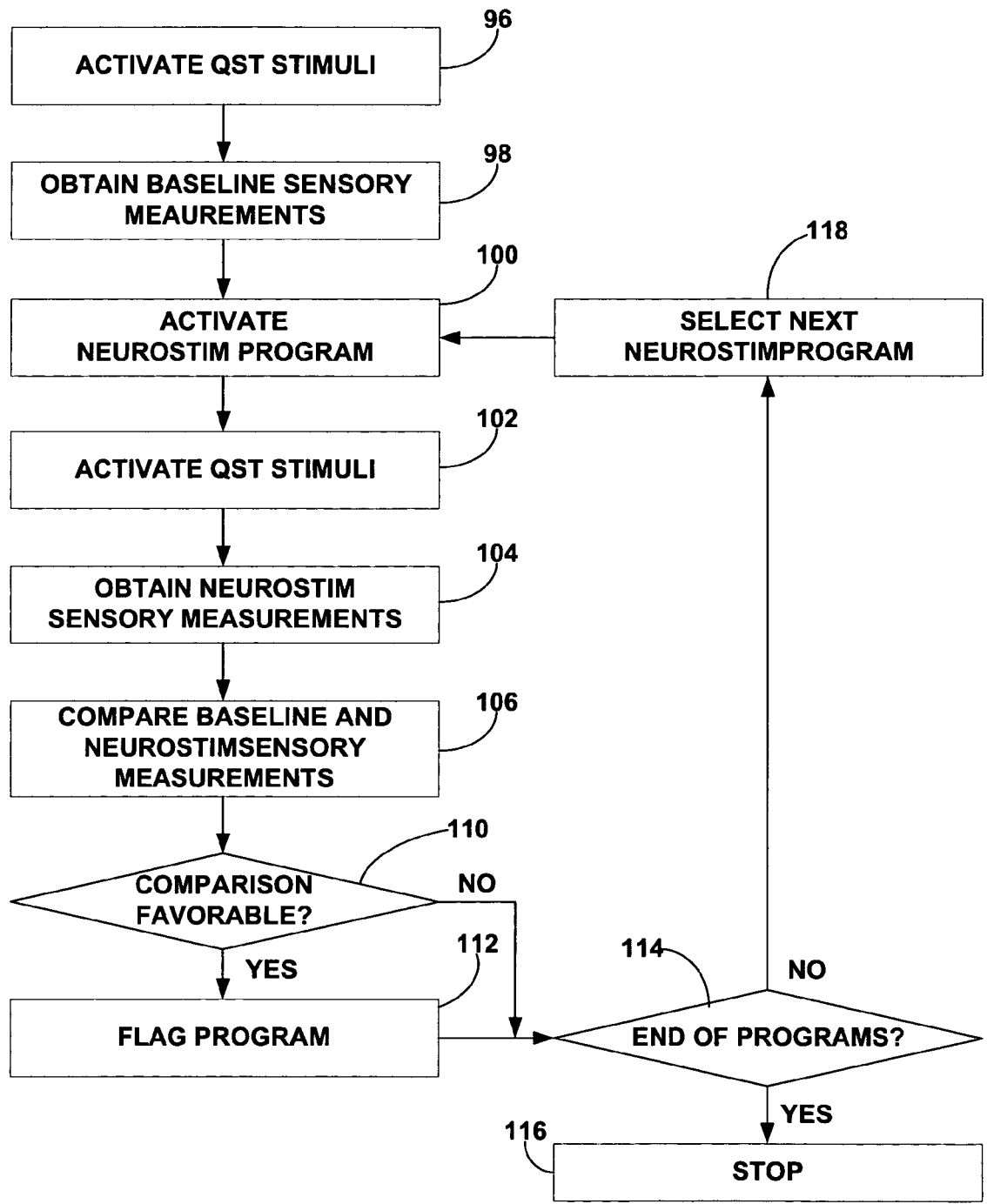
FIG. 6 is a flow diagram illustrating a technique for evaluating patient sensory response to rate neuromodulation efficacy.

FIG. 6 is a flow diagram illustrating a technique for evaluating patient sensory response to rate neuromodulation efficacy. The technique may be implemented by system 10 of FIG. 1. As shown in FIG. 6, upon activating the QST stimuli (96), baseline sensory measurements are obtained from the patient and recorded (98). Again, the external sensory stimulation may take a variety of forms, including electrical stimulation, vibratory stimulation, thermal stimulation, tactile stimulation or a succession of different stimulation types. The baseline sensory measurements may include perception thresholds, tolerance limits or other measurements.

To evaluate the change in patient sensory response caused by neurostimulation, a selected neurostimulation program is activated (100), e.g., by clinician programmer 14. The, the QST stimuli are then activated (102), and neurostimulation sensory test measurements are obtained (104) in the presence of sensory stimulation and neurostimulation, and recorded. Upon comparison of the baseline and neurostimulation sensory test measurements (106), clinician programmer 14 determines whether the comparison is favorable to neurostimulator implantation.

In particular, if the sensory measurements change favorably upon application of a neurostimulation program, the program may be identified as potentially efficacious. For example, if the comparisons are favorable (110), the program is flagged (112). The comparison may simply be an indication of whether a perception threshold is increased or decreased relative to the baseline perception threshold. Similarly, the rating may reflect whether the patient can tolerate more or less pain or other stimulation. An increased sensory perception or sensory tolerance limit may be viewed as favorable. Even if a program is flagged based on a favorable QST result, it should be evaluated for clinical result, e.g., actual relief of symptoms.

Figure 7:
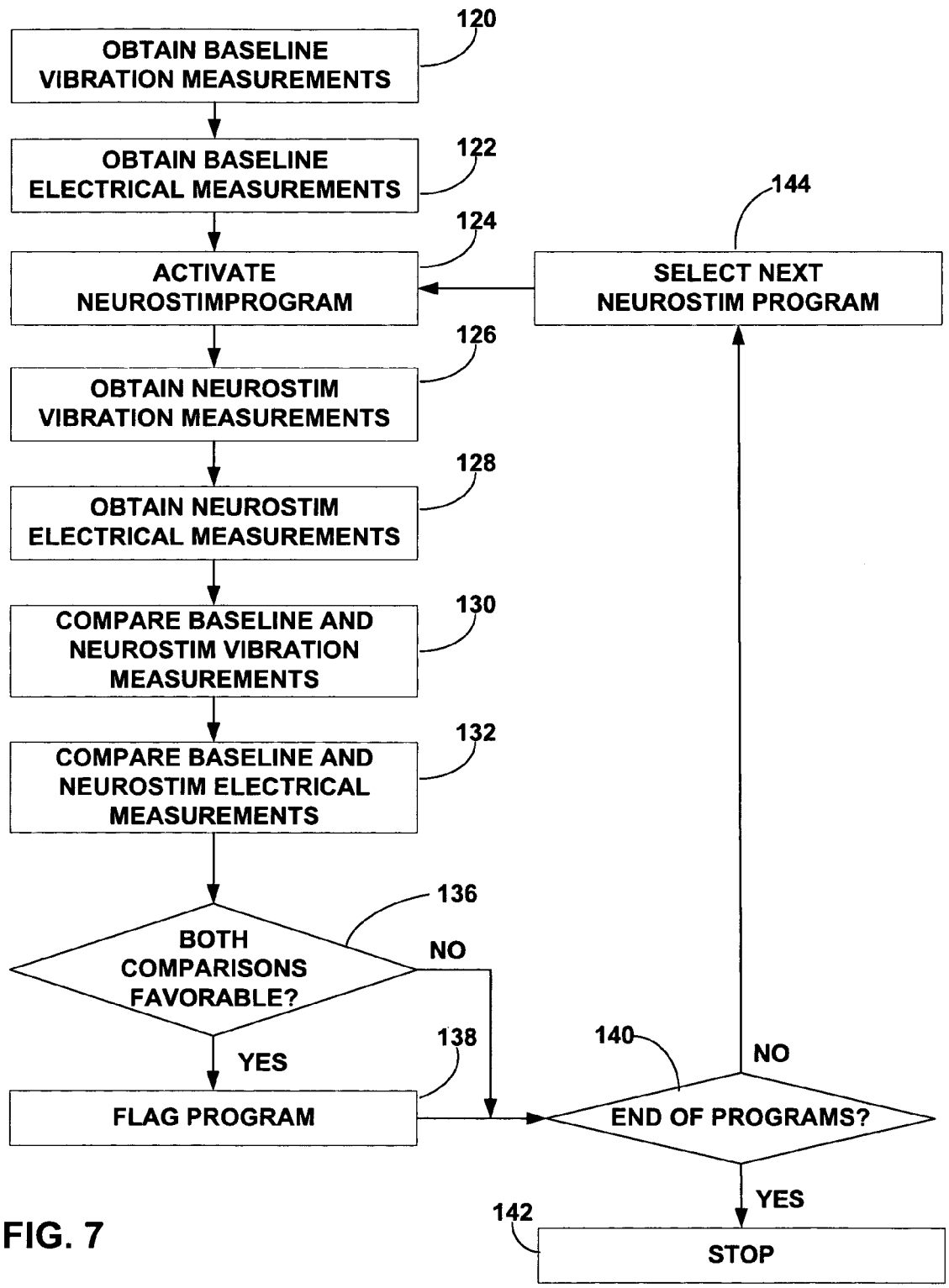
FIG. 7 is a flow diagram illustrating another technique for evaluating patient sensory response to rate neuromodulation efficacy.

In particular, if a patient's perception threshold or stimulation tolerance limit is increased during application of neurostimulation, the effect of the neurostimulation program on the sensory response of the patient may be diagnostic of short-term neurostimulation success and prognostic of long-term success. Multiple neurostimulation programs may be evaluated for their effect on the patient sensory response, and flagged if they have a favorable effect. Once the end of the programs is reached (114), the process stops (116). If the end of the programs has not been reached, the process repeats by selecting the next neurostimulation program (118). The results can be stored in clinician programmer 14 to aid a clinician in not only determining whether implantation is advisable, but also selecting a particular neurostimulation program once implantation is done FIG. 7 is a flow diagram illustrating another technique for evaluating patient sensory response to rate neuromodulation efficacy. The technique of FIG. 7 corresponds generally to the technique of FIG. 6, but involves the analysis of sensory response for two different types of external sensory stimulation. For example, the effects of neurostimulation on patient sensory response to electrical stimulation and vibratory stimulation may provide a more specific and selective indication of the likely efficacy of neuromodulation. Rather than focusing on only a single type of external sensory stimulation, a requirement that neurostimulation have a favorable effect on sensory response for two or more different types of stimulation provides a correlative relationship that increases the confidence of the decision to implant a neurostimulator. In the example of FIG. 7, electrical and vibratory stimulation are illustrated as two types of stimulation.

In some embodiments, a second type of stimulation may be applied only in the event favorable results are not obtained with the first type of stimulation by a sufficiently wide margin. For example, if neurostimulation causes a substantial favorable change in patient sensory response to external electrical stimulation, a prediction may be made that the neurostimulation is likely to be efficacious, thereby warranting implantation. If the neurostimulation causes a smaller change, e.g., below a predetermined threshold difference, then the clinician may elect to further investigate the effects of the neurostimulation on a second type of external sensory stimulation, such as vibratory stimulation. If the neurostimulation causes a substantial change in patient sensory response to the second type of stimulation, e.g., vibratory stimulation, a prediction of efficacy may be made with greater confidence. In this case, measurement of changes in patient sensory responses to two different types of external sensory stimulation in the presence of neurostimulation may provide greater selectivity and specificity in the prediction.

As shown in FIG. 7, baseline vibration measurements are obtained (120) during application of vibratory stimulation to the patient and in the absence of neurostimulation. The baseline vibration measurements may include a perception threshold. Then, baseline electrical measurements may be obtained (122). The baseline electrical measurements may include a perception threshold and a pain tolerance limit. Upon activation of a neurostimulation program, test measurements are obtained for the vibration and electrical stimulation (126, 128). Upon comparison of the baseline and neurostimulation test vibration and electrical measurements (130, 132), if both comparisons are favorable, the neurostimulation program under study is flagged (138). If the end of programs has been reached (140), the process stops (142). Alternatively, the next program is selected (144).

According to another embodiment, baseline vibration measurements are obtained during application of vibratory stimulation to the patient. Then, baseline electrical measurements may be obtained. Upon activation of a neurostimulation program, similar test measurements are obtained for the vibration, and the baseline and neurostimulation vibration test measurements are compared. If the comparison is favorable, then electrical measurements may be taken for patient sensory response to external electrical stimulation. If the vibratory comparison is not favorable, however, the clinician or patient may simply forego the electrical measurement and conclude that the applicable neurostimulation program is not likely to be efficacious. As a variation, the process may take the baseline electrical measurement and neurostimulation measurement only if the vibratory measurements are not favorable. In another embodiment, if a patient's visual analog score (VAS) score rises with neurostimulation, then the process can be terminated without testing other measurements such as electrical or vibratory external sensory stimulation.

Figure 8:
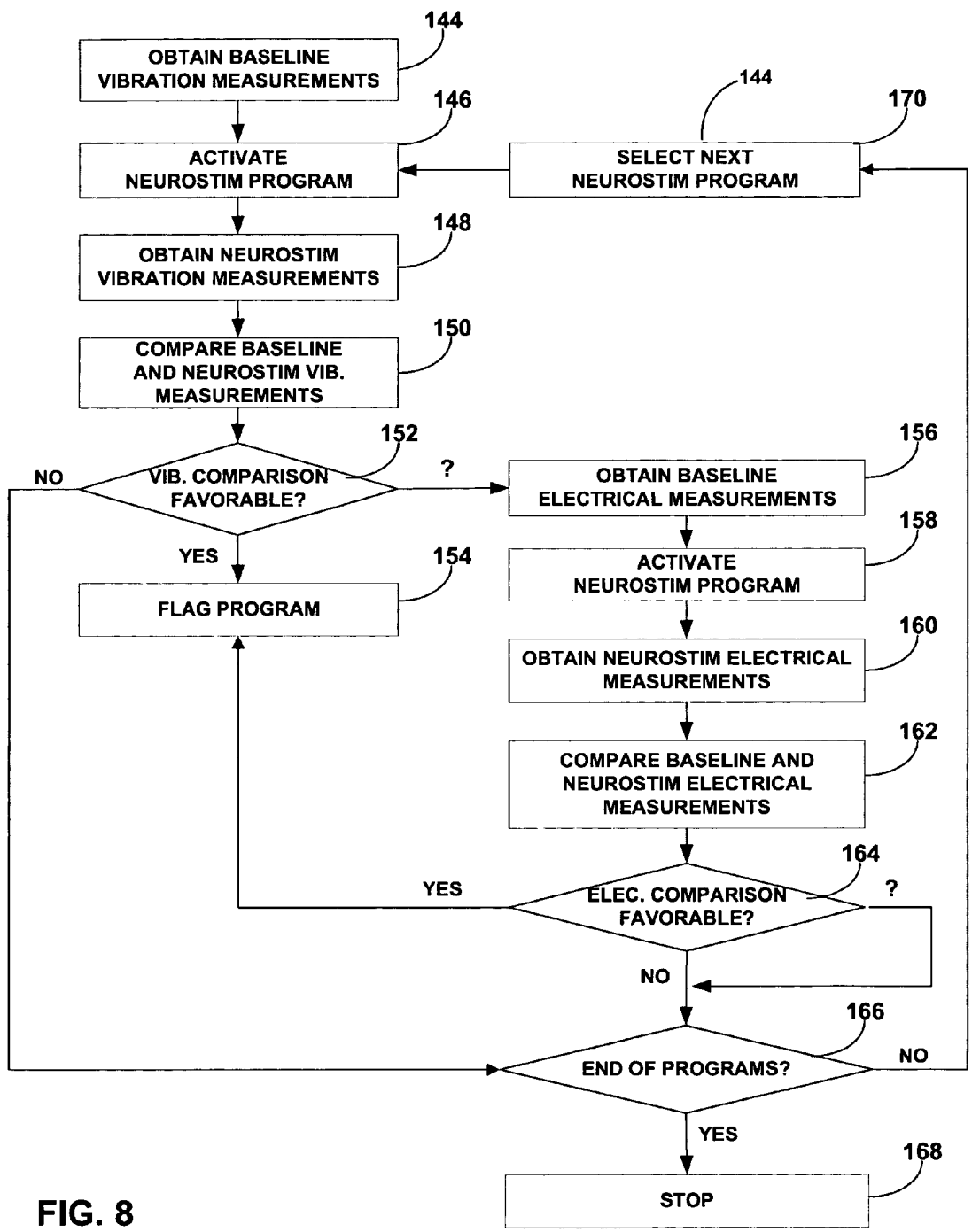
FIG. 8 is a flow diagram illustrating an additional technique for evaluating patient sensory response to rate neuromodulation efficacy.

FIG. 8 is a flow diagram illustrating an additional technique, as described above, for evaluating patient sensory response to rate neuromodulation efficacy. As shown in FIG. 8, the technique involves obtaining baseline vibration sensory measurements (patient response to vibratory stimulation) (144), activating a selected neurostimulation program (146), obtaining vibration sensory test measurements during neurostimulation (148), and comparing the baseline and neurostimulation vibration sensory test measurements (150). If the comparison is favorable and definitive (152), i.e., neurostimulation changes the patient sensory response favorably by a sufficiently wide margin, the program is flagged (154) as being potentially efficacious. If the comparison is not favorable, the next program is selected for evaluation (166, 170) unless all programs of interest have been investigated (168).

If the comparison is favorable but not definitive, electrical measurements are taken. Specifically, the technique then involves obtaining baseline electrical sensory measurements (patient response to external electrical stimulation), i.e., in the absence of neuromodulation therapy (156), activating neurostimulation (158), and obtaining neurostimulation electrical test measurements (160), and comparing the baseline and neurostimulation electrical test measurement (162). If the comparison is favorable, the program is flagged (154). If the program is favorable but not definitive, or unfavorable, the next program is selected (166, 170). The process stops (168) when the end of the programs is reached (166). Although the first and second types of stimulation described with respect to FIG. 8 are vibratory and electrical stimulation, electrical could be tried first rather than vibratory, and other types of stimulation could possibly be used in place of electrical or vibratory stimulation.

Application of external sensory stimulation in the form of electrical, vibratory, tactile, thermal, and chemical stimulation have been described herein for purposes of illustration. In addition, a number of measurements, such as perception thresholds and tolerance limits, have been described. Changes in patient sensory response to electrical and vibratory stimulation may correlate particularly well to short-term and long-term efficacy of neurostimulation therapy such as spinal cord stimulation (SCS) for pain relief. However, a system as described herein may be configured to apply other types of stimulation, and obtain and analyze a variety of different measurements indicative of patent sensory response. Further examples of external sensory types and appropriate patient sensory response measurements will now be described in further detail.

A system as described herein may be adapted to make use of the different stimulation types and measurements to predict short-term and long-term efficacy of an implantable neurostimulator for a given patient. Examples of different types of external sensory stimulation and possible patient sensory response measurements are described below. For electrical stimulation, vibratory stimulation, or thermal stimulation, measurements may include nonpainful perception thresholds, pain perception thresholds, and pain tolerance limits.

Alternative measurements may be obtained in the form of pain ratings, e.g., where the patient ranks pain caused by a given level of electrical or thermal stimulation on a numerical scale, or where the patient uses a visual analog scale (VAS). The patient also may use word rankings of pain such as no pain, modest pain, mild pain, noticeable pain, severe pain, and the like. Other possible rating scales, serving as pain measurement vehicles, include reference to the McGill pain rating scale, activities of daily living metrics, reference to established pain inventories such as the Oswestry, SF-36, or Minnesota Multiphasic Personality Inventory (MMPI) indices. For tactile stimulation, tactile measurements may include perception thresholds such as pin prick or cotton wisp sensations, and discrimination of multiple tactile point sources. These tests may use other QST devices, such as von Frey filaments. In each case, regardless of the precise type of stimulation and type of measurement, a correlation may be discovered between a change in the measurement due to neurostimulation and the likely short-term or long-term efficacy of neuromodulation. In each case, a rating engine may be designed to rate efficacy based on the resulting patient report information.

For another possible test, it might not be necessary to implant a trial SCS lead. It may be possible to provide TENS at a site, and also perform all the sensory tests at other sites, but probably in the same dermatome. This may be especially good as a trial for angina. TENS works well for angina, usually. Spinal cord stimulation (SCS) may also work. In some applications, patients can be selected for SCS for angina (and implant without screening) if TENS is performed (and it helps the angina) and the sensory tests are also changed.

Figure 9:
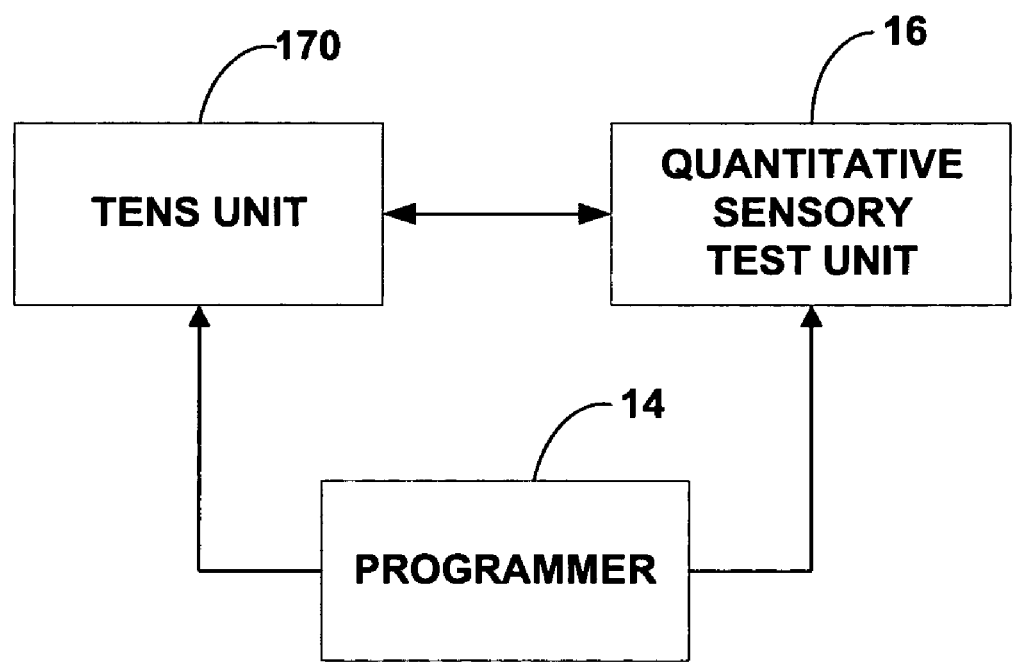
FIG. 9 is a block diagram illustrating another system for evaluating patient sensory response to rate neuromodulation efficacy.

FIG. 9 is a block diagram illustrating another system for evaluating patient sensory response to rate neuromodulation efficacy. The system includes a programmer 14 and a QST unit 16, as in the example of FIG. 1. As shown in FIG. 9, however, instead of an implantable trial neurostimulator, the system makes use of a TENS unit 170 to deliver the cutaneous neurostimulation used in evaluating changes in patient sensory response to external sensor stimulation delivered by QST unit 16. TENS unit 170 may be advantageous because it does not require surgical implantation to be performed as part of the screening process; rather, the TENS unit 170 includes electrodes that are affixed to the surface of the patient's skin.

Figure 10:
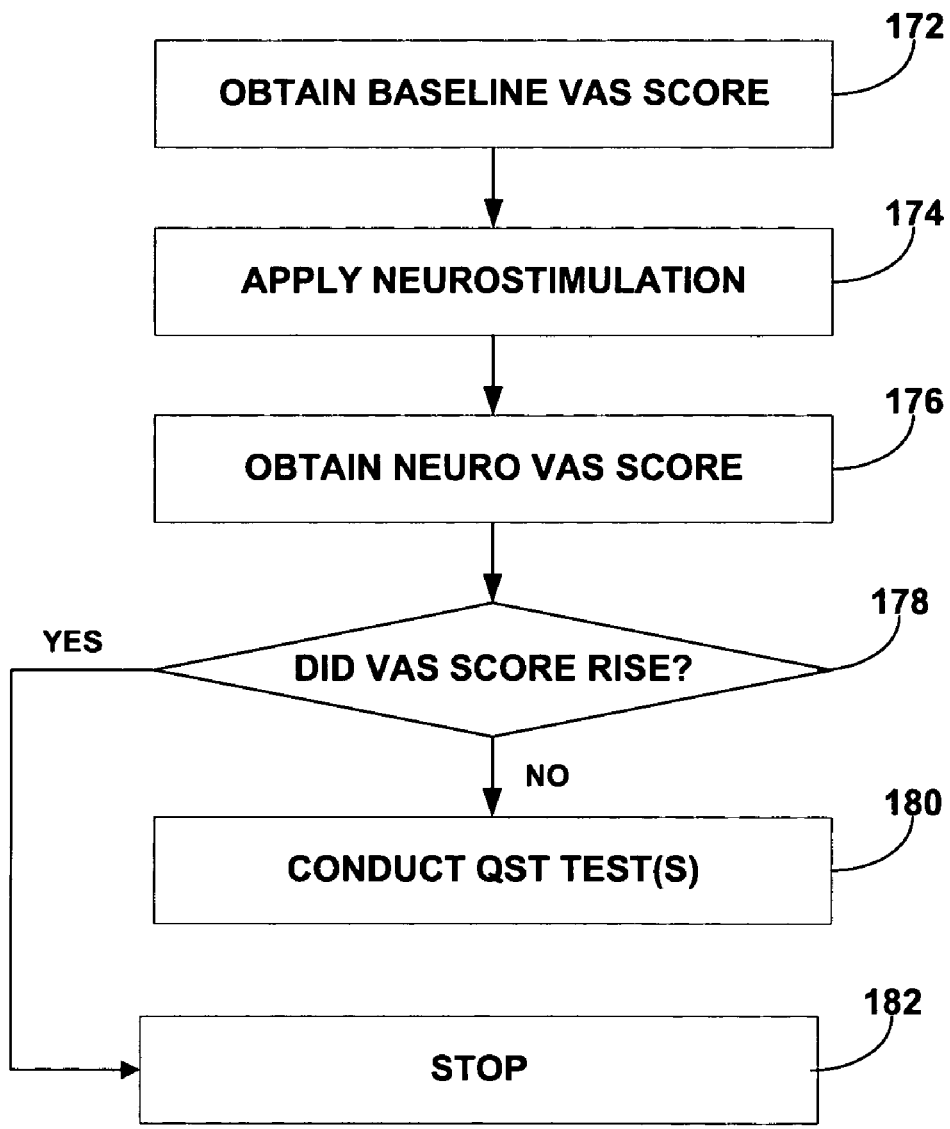
FIG. 10 is a flow diagram illustrating use of a visual analog scale (VAS) test as a threshold determination for analysis of sensory response.

FIG. 10 is a flow diagram illustrating use of a visual analog scale (VAS) test as a threshold determination for analysis of sensory response. As shown in FIG. 10, before deciding whether to evaluate changes in patient sensory response, neurostimulation is applied to the patient to obtain a comparison of VAS scores, before and during neurostimulation. If the VAS score actually rises during neurostimulation, it is unlikely that neuromodulation will be efficacious.

Accordingly, the various patient sensory response tests described herein can simply be avoided if the VAS score rises with neurostimulation. As shown in FIG. 10, this process involves obtaining a baseline VAS score (172), applying neurostimulation (174), obtaining a VAS score during neurostimulation (176), and determining whether the VAS score rose during neurostimulation (178). If so, the test is stopped (182). If the VAS score improved, however, the QST test or tests can be completed (180) to evaluate possible neuromodulation efficacy.

EXAMPLE

A pilot study was conducted using both a pain tolerance test (PTT) test and a vibrational threshold test at four hospitals. The equipment used was the NervScan™ LLC device, commercially available from Neurotron, Inc., of Baltimore, Md., USA, for PTT, and the TSA II NeuroSensory Analyzer, commercially available from Medoc Advanced Medical Systems, of Chapel Hill, N.C., USA, for vibration threshold measurements. Testing sites were the fingers and toes of three limbs, using the same dermatomes as the sites of the worst chronic neuropathic pain, and tests were done at baseline and after one week of trial SCS, with stimulation on. Patients had chronic radicular neuropathy or complex regional pain syndrome. Out of 10 patients with PTT data, 4 out of 5 patients who achieved clinical success, i.e., had a complete SCS system implanted, had their PTT amplitude increase with SCS, versus only 2 of 5 who did not see sufficient pain relief to have a complete SCS system implanted.

Out of 10 patients with vibration threshold measurements at baseline and after a week of trial SCS, all six of six patients who achieved clinical success had their vibration threshold amplitude rise with SCS, versus only two of four patients who had clinical failure at SCS trial. These were trends only, and not statistically significant. However, it was discovered that if one criteria is added to using these tests, the results can be improved. If the test is not applied in cases where patients report that their pain actually increased with trial SCS (measured by VAS), then the specificity of the test improves for those not achieving clinical success, and thus not getting an internalized, fully-implanted, system. Thus, the combination of two QST tests and a clinical trial outcome report (VAS, subjective, from patient), may allow the test to have improved sensitivity and specificity. In the above cases, by excluding those patients with pain rising from SCS, the sensitivity becomes 80% for PTT and 100% for vibration threshold; and the specificity is 100% for both tests.

Certain aspects of the invention may be embodied as a computer-readable medium comprising instructions for causing a programmable processor to carry out procedures in support of the techniques described herein. For example, software, firmware and/or hardware may be provided to facilitate application of external sensory stimulation and neuromodulation, reporting of sensory response, and rating of efficacy.

Various embodiments of the invention have been described. However, one skilled in the art will appreciate that various additions and modifications can be made to these embodiments without departing from the scope of the invention. These and other embodiments are within the scope of the following claims.

The invention claimed is:

1. A method comprising:
applying a first type of external sensory stimulation to a patient;
obtaining a baseline measurement of patient sensory response to the first type of external sensory stimulation;
applying a second type of external sensory stimulation to a patient;
obtaining a baseline measurement of patient sensory response to the second type of external sensory stimulation;
applying neuromodulation therapy to the patient simultaneously with application of the first type of external sensory stimulation;
obtaining a test measurement of patient sensory response to the first type of external sensory stimulation during simultaneous application of the first type of external sensory stimulation and the neuromodulation therapy;
applying neuromodulation therapy to the patient simultaneously with application of the second type of external sensory stimulation;
obtaining a test measurement of patient sensory response to the second type of external sensory stimulation during simultaneous application of the second type of external sensory stimulation and the neuromodulation therapy;
evaluating efficacy of the neuromodulation therapy based on a comparison of the baseline measurements and the test measurements.

2. The method of claim 1, wherein evaluating efficacy includes at least one of evaluating diagnostic efficacy and prognostic efficacy.

3. The method of claim 1, wherein applying neuromodulation therapy includes at least one of applying neurostimulation therapy and drug delivery therapy.

4. The method of claim 3, wherein the drug delivery therapy includes at least one of delivery of a drug orally, by injection, by implantable drug pump, by external drug pump, and by transdermal patch.

5. The method of claim 1, wherein applying neuromodulation therapy includes applying neurostimulation therapy via one or more implanted neurostimulation leads.

6. The method of claim 1, wherein applying neuromodulation therapy includes applying neurostimulation therapy by transcutaneous electrical nerve stimulation.

7. The method of claim 1, wherein the external sensory stimulation includes at least one of tactile, vibrational, thermal, pressure, electrical, and chemical stimulation.

8. The method of claim 1, wherein the patient sensory response includes at least one of a perception threshold, a pain threshold, and a tolerance limit.

9. The method of claim 8, wherein the patient report includes input indicated in a visual analog scale format.

10. The method of claim 1, wherein the patient sensory response includes a patient report relating to perceived pain relief.

11. The method of claim 1, further comprising performing the method in one of a clinic and a patient home.

12. The method of claim 1, further comprising using an integrated device to apply at least one of the first and second types of external sensory stimulation and to control the application of the neurostimulation therapy.

13. The method of claim 1, further comprising using a device to control both a quantitative sensory testing device to apply at least one of the first and second types of external sensory stimulation and a neuromodulation device to apply the neuromodulation therapy.

14. The method of claim 1, wherein one of the first and second types of external sensory stimulation includes electrical stimulation.

15. The method of claim 1, wherein one of the first and second types of external sensory stimulation includes vibratory stimulation.

16. The method of claim 1, wherein the first type of external sensory stimulation includes vibratory stimulation, and the second type of external sensory stimulation includes electrical stimulation.

17. The method of claim 1, wherein applying neuromodulation therapy includes applying different neurostimulation programs, the method further comprising obtaining multiple test measurements of patient sensory response to the first and second types of external sensory stimulation during application of the different neurostimulation programs, and identifying favorable neurostimulation programs based on the comparison of the baseline measurements and the test measurements for the first and second types of external sensory stimulation.

18. The method of claim 1, further comprising repeating the measurements following implant of an implantable neurostimulator in the patient.

19. The method of claim 18, wherein the application of a drug includes at least one of topical application and intraspinal application of the drug.

20. The method of claim 1, wherein the external sensory stimulation includes application of a drug to the patient.

21. A system comprising:
a first sensory stimulation unit to apply a first type of external sensory stimulation to a patient;
a second sensory stimulation unit to apply a second type of external sensory stimulation to the patient;
a neuromodulation unit to apply neuromodulation therapy to the patient;
a device to obtain a baseline measurement of patient sensory response to the first type of external sensory stimulation without application of the neuromodulation therapy, obtain a baseline measurement of patient sensory response to the second type of external sensory stimulation without application of the neuromodulation therapy, obtain a test measurement of patient sensory response to simultaneous application of the first type of external sensory stimulation and the neuromodulation therapy, obtain a test measurement of patient sensory response to simultaneous application of the second type of external sensory stimulation and the neuromodulation therapy, and evaluate efficacy of the neuromodulation therapy based on a comparison of the baseline measurements and the test measurements.

22. The system of claim 21, wherein the first and second stimulation units are integrated within a common stimulation unit.

23. The system of claim 21, wherein the device evaluates at least one of diagnostic efficacy and prognostic efficacy.

24. The system of claim 21, wherein the neuromodulation therapy includes at least one of neurostimulation therapy and drug delivery therapy.

25. The system of claim 24, wherein the drug delivery therapy includes one of delivery of a drug by injection, by implantable drug pump, by external drug pump, and by transdermal patch.

26. The system of claim 21, wherein the neuromodulation unit includes an implantable neurostimulation unit.

27. The system of claim 21, wherein the neuromodulation unit includes a transcutaneous electrical nerve stimulation unit.

28. The system of claim 21, wherein the device includes a programmer that controls the neuromodulation unit.

29. The system of claim 28, wherein the programmer also controls the sensory stimulation unit.

30. The system of claim 21, wherein the external sensory stimulation includes at least one of tactile, vibrational, thermal, pressure, electrical, and chemical stimulation.

31. The system of claim 21, wherein one of the first and second types of external sensory stimulation includes electrical stimulation.

32. The system of claim 21, wherein one of the first and second types of external sensory stimulation includes vibratory stimulation.

33. The system of claim 21, wherein the first type of external sensory stimulation includes vibratory stimulation and the second type of external sensory stimulation includes electrical stimulation.

34. The system of claim 21, wherein the patient sensory response includes at least one of a perception threshold, a pain threshold, and a tolerance limit.

35. The system of claim 21, wherein the patient sensory response includes a patient report relating to perceived pain relief.

36. The system of claim 35, wherein the patient report includes input indicated in a visual analog scale format.

37. The system of claim 21, wherein the neuromodulation unit applies different neurostimulation programs, and the device obtains multiple test measurements of patient sensory response to the first and second types of external sensory stimulation during application of the different neurostimulation programs, and identifies favorable neurostimulation programs based on the comparison of the baseline measurements and the test measurements for the first and second types of external sensory stimulation.

38. The system of claim 21, wherein the external sensory stimulation includes application of a drug to the patient.

39. The system of claim 38, wherein the application of a drug includes at least one of topical application and intraspinal application of the drug.

40. A method comprising:
applying a first type of external sensory stimulation to a patient;
obtaining a baseline measurement of patient sensory response to the first type of external sensory stimulation;
applying a second type of external sensory stimulation to a patient;
obtaining a baseline measurement of patient sensory response to the second type of external sensory stimulation;
applying neuromodulation therapy to the patient simultaneously with application of the first type of external sensory stimulation;
obtaining a test measurement of patient sensory response to the first type of external sensory stimulation during simultaneous application of the first type of external sensory stimulation and the neuromodulation therapy;
evaluating efficacy of the neuromodulation therapy based on a comparison of the baseline measurements and the test measurements for the first type of external sensory stimulation;
if the evaluation indicates efficacy, applying neuromodulation therapy to the patient simultaneously with application of the second type of external sensory stimulation;
obtaining a test measurement of patient sensory response to the second type of external sensory stimulation during simultaneous application of the second type of external sensory stimulation and the neuromodulation therapy; and
evaluating efficacy of the neuromodulation therapy based on a comparison of the baseline measurements and the test measurements for the first and second types of external sensory stimulation.

41. A system comprising:
a first sensory stimulation unit to apply a first type of external sensory stimulation to a patient;
a second sensory stimulation unit to apply a second type of external sensory stimulation to the patient;
a neuromodulation unit to apply neuromodulation therapy to the patient;
a device to obtain a baseline measurement of patient sensory response to the first type of external sensory stimulation without application of the neuromodulation therapy, obtain a baseline measurement of patient sensory response to the second type of external sensory stimulation without application of the neuromodulation therapy, obtain a test measurement of patient sensory response to simultaneous application of the first type of external sensory stimulation and the neuromodulation therapy, evaluate efficacy of the neuromodulation therapy based on a comparison of the baseline measurements and the test measurements,
wherein device, if the evaluation indicates efficacy, obtains a test measurement of patient sensory response to simultaneous application of the second type of external sensory stimulation and the neuromodulation therapy, and evaluating efficacy of the neuromodulation therapy based on a comparison of the baseline measurements and the test measurements for the first and second types of external sensory stimulation.

* * * * *